United States Patent
Chaplin et al.

(12)

(10) Patent No.: US 11,129,686 B2
(45) Date of Patent: Sep. 28, 2021

(54) DRIVING ARRANGEMENT FOR ARTICULATING A SURGICAL INSTRUMENT

(71) Applicant: CMR Surgical Limited, Cambridge (GB)

(72) Inventors: Ben Robert Chaplin, Cambridge (GB); Ross Hamilton Henrywood, Cambridge (GB); Archie John Ralph Lodge, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 233 days.

(21) Appl. No.: 16/340,254

(22) PCT Filed: Oct. 6, 2017

(86) PCT No.: PCT/GB2017/053038
§ 371 (c)(1),
(2) Date: Apr. 8, 2019

(87) PCT Pub. No.: WO2018/069679
PCT Pub. Date: Apr. 19, 2018

(65) Prior Publication Data
US 2020/0038127 A1 Feb. 6, 2020

(30) Foreign Application Priority Data
Oct. 14, 2016 (GB) ...................... 1617448

(51) Int. Cl.
*A61B 34/30* (2016.01)
*A61B 34/00* (2016.01)
(Continued)

(52) U.S. Cl.
CPC .......... *A61B 34/71* (2016.02); *A61B 17/0218* (2013.01); *A61B 17/072* (2013.01);
(Continued)

(58) Field of Classification Search
CPC ............ A61B 17/072; A61B 17/07207; A61B 17/00234; A61B 2017/00477;
(Continued)

(56) References Cited

U.S. PATENT DOCUMENTS 5,562,702 A * 10/1996 Huitema .......... A61B 17/07207
600/564
5,716,352 A * 2/1998 Viola ................ A61B 17/00234
128/898

(Continued)

FOREIGN PATENT DOCUMENTS

CN 104116547 A 10/2014
EP 3040045 A1 7/2016
(Continued)

OTHER PUBLICATIONS

Haegeman, Marc, International Search Report issued in application No. PCT/GB2017/053038 completion date Dec. 20, 2017, dated Jan. 4, 2018, 2 pages.

(Continued)

*Primary Examiner* — Scott A Smith
(74) *Attorney, Agent, or Firm* — King & Spalding LLP (57) ABSTRACT

A robotic surgical instrument comprising a shaft, a first end effector element, an articulation connecting the first end effector element to a distal end of the shaft, the first end effector element being movable relative to the articulation, and a drive mechanism at a proximal end of the shaft. The drive mechanism comprises a first actuator connected to the first end effector element by a first pair of driving elements. The first pair of driving elements are configured such that a tension force applied by the first actuator to a first one of the first pair of driving elements causes the first end effector element to move relative to the articulation in a first motion direction, and the tension force applied to a second one of the first pair of driving elements causes the first end effector (Continued)

element to move relative to the articulation in a second motion direction. The first one of the first pair of driving elements has a first path between the first actuator and the first end effector element, and the second one of the first pair of driving elements has a second path between the first actuator and the first end effector element. The first path has a lower tension force loss than the second path such that the first motion direction transfers a greater proportion of the tension force to the first end effector element than the second motion direction.

20 Claims, 7 Drawing Sheets

(51) Int. Cl.
*A61B 17/02* (2006.01)
*A61B 17/072* (2006.01)
*A61B 17/128* (2006.01)
*A61B 17/00* (2006.01)
*A61B 17/29* (2006.01)

(52) U.S. Cl.
CPC .......... *A61B 17/1285* (2013.01); *A61B 34/30* (2016.02); *A61B 17/00234* (2013.01); *A61B 17/29* (2013.01); *A61B 34/70* (2016.02); *A61B 2017/00477* (2013.01); *A61B 2017/07271* (2013.01); *A61B 2017/07285* (2013.01); *A61B 2017/2927* (2013.01); *A61B 2017/2939* (2013.01); *A61B 2034/305* (2016.02); *A61B 2034/715* (2016.02)

(58) Field of Classification Search
CPC .......... A61B 2017/07214; A61B 34/30; A61B 34/70; A61B 34/71; A61B 2034/305; A61B 2034/715; A61B 17/29; A61B 2017/2927; A61B 2017/2939; A61B 34/37; A61B 34/77
USPC .... 227/19, 175.1, 176.1; 606/1, 51, 52, 130, 606/174, 205, 208, 219; 74/490.05, 74/490.06
See application file for complete search history.

(56) References Cited

U.S. PATENT DOCUMENTS

| | | | |
|---|---|---|---|
| 5,792,135 A * | 8/1998 | Madhani | A61B 17/00234 606/1 |
| 6,197,017 B1 * | 3/2001 | Brock | B25J 3/04 414/5 |
| 6,206,903 B1 * | 3/2001 | Ramans | A61B 17/29 606/205 |
| 6,364,888 B1 * | 4/2002 | Niemeyer | A61B 1/00149 606/130 |
| 6,371,952 B1 * | 4/2002 | Madhani | A61B 17/00234 606/1 |
| 6,394,998 B1 * | 5/2002 | Wallace | A61B 34/71 606/1 |
| 6,554,844 B2 * | 4/2003 | Lee | A61B 34/30 606/130 |
| 6,676,684 B1 * | 1/2004 | Morley | A61B 34/71 606/205 |
| 6,840,938 B1 * | 1/2005 | Morley | A61B 18/1445 606/51 |
| 7,331,967 B2 * | 2/2008 | Lee | A61B 34/71 600/407 |
| 7,398,707 B2 * | 7/2008 | Morley | A61B 17/062 74/490.06 |
| 7,699,835 B2 * | 4/2010 | Lee | A61B 34/35 606/1 |
| 7,935,130 B2 * | 5/2011 | Williams | A61B 34/37 606/208 |
| 8,398,634 B2 * | 3/2013 | Manzo | A61B 34/30 606/52 |
| 8,597,182 B2 * | 12/2013 | Stein | A61B 34/37 600/214 |
| 8,821,480 B2 * | 9/2014 | Burbank | A61B 34/30 606/1 |
| 9,050,119 B2 * | 6/2015 | Devengenzo | A61B 34/37 |
| 2007/0208375 A1 * | 9/2007 | Nishizawa | A61B 34/71 606/205 |
| 2007/0288044 A1 * | 12/2007 | Jinno | A61B 34/70 606/174 |
| 2010/0011901 A1 | 1/2010 | Burbank | |
| 2011/0106145 A1 * | 5/2011 | Jeong | A61B 34/77 606/205 |
| 2011/0282491 A1 | 11/2011 | Prisco et al. | |
| 2015/0127045 A1 * | 5/2015 | Prestel | A61B 34/71 606/208 |

FOREIGN PATENT DOCUMENTS

| | | |
|---|---|---|
| JP | 2014-193417 | 10/2014 |
| WO | WO 2014/012780 A1 | 1/2014 |

OTHER PUBLICATIONS

International Search Report issued for International Patent Application No. GB1617448.4 dated Mar. 6, 2017, 3 pages.
Notice of Reason(s) for Refusal issued in Japanese Patent Application No. 2019-519987, dated Jul. 20, 2021, 4 pages total including translation.

* cited by examiner

DRIVING ARRANGEMENT FOR ARTICULATING A SURGICAL INSTRUMENT

BACKGROUND

Figure 1:
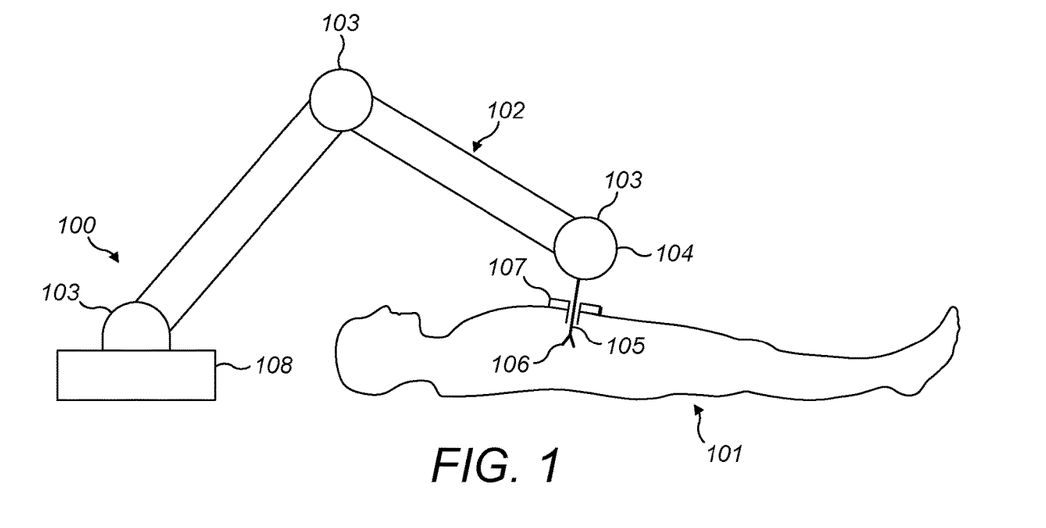
FIG. 1 illustrates a surgical robot performing a surgical procedure.

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

Figure 2:
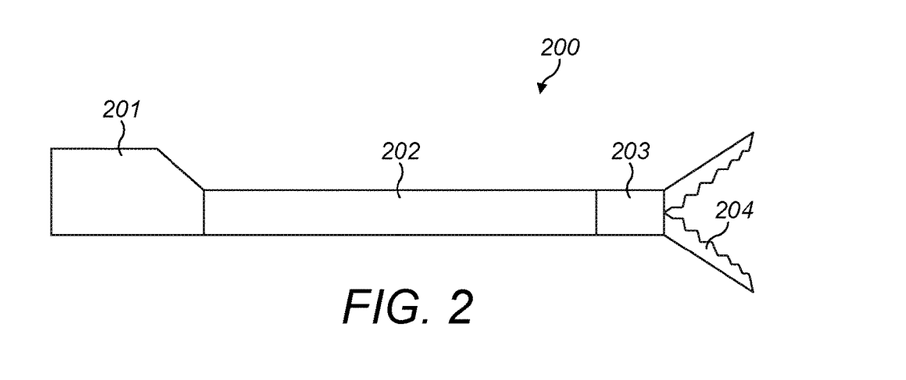
FIG. 2 illustrates a known surgical instrument.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

Figure 3:
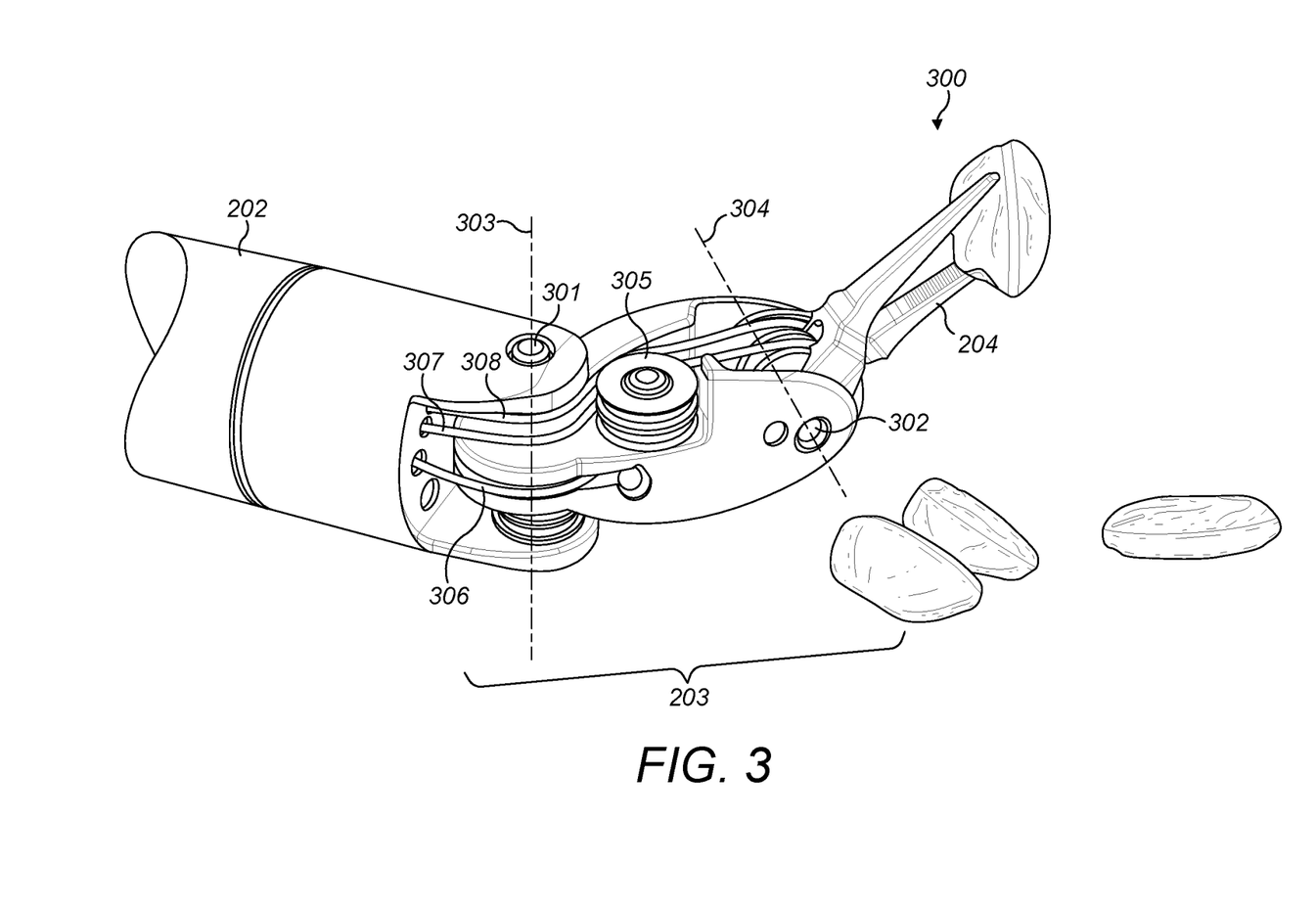
FIG. 3 illustrates a known arrangement of an articulated end effector of a surgical instrument.

Robotic surgical instruments are long and have a narrow external diameter. Typically, their length is of the order of 40 cm and their diameter 8 mm. FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. By rotating the jaws in opposing directions about the yaw axis, they are able to grip and release tissue. The joints are driven by cables 306, 307 and 308.

Tension applied to cables 307 and 308 in base 201 causes rotation of the jaws of the end effector about yaw axis 304. The long, narrow nature of the instrument results in there being a limited moment available to amplify the tension force applied to the cables 307 and 308 in the base 201. The force that can be applied to each cable is limited by its construction and how it is secured at its terminations. Thus, the force with which the jaws of the end effector are able to grip objects between them is limited. Increasing the available gripping force of the end effector is desirable to aid the surgeon in manipulating tissue, performing cutting operations, and grasping other implements such as needles.

Furthermore, it is desirable to reduce the external diameter of the instrument in order to minimise the size of the incision through the skin of the patient and minimise disruption inside the patient's body. This reduces the size of cables which can be accommodated by the instrument shaft and articulation, and hence further reduces the force which can be applied to the end effectors.

It is desirable to satisfy the competing needs of reducing the external diameter of the instrument and increasing the gripping force of the jaws of an end effector.

SUMMARY OF THE INVENTION

According to an aspect of the invention, there is provided a robotic surgical instrument comprising: a shaft; a first end effector element; an articulation connecting the first end effector element to a distal end of the shaft, the first end effector element movable relative to the articulation; and a drive mechanism at a proximal end of the shaft comprising a first actuator, the first actuator being connected to the first end effector element by a first pair of driving elements, the first pair of driving elements being configured such that a tension force applied by the first actuator to a first one of the first pair of driving elements causes the first end effector element to move relative to the articulation in a first motion direction, and the tension force applied to a second one of the first pair of driving elements causes the first end effector element to move relative to the articulation in a second motion direction; wherein the first one of the first pair of driving elements has a first path between the first actuator and the first end effector element, and the second one of the first pair of driving elements has a second path between the first actuator and the first end effector element, the first path having a lower tension force loss than the second path such that the first motion direction transfers a greater proportion of the tension force to the first end effector element than the second motion direction.

The robotic surgical instrument may further comprise a second end effector element; the articulation connecting the second end effector element to the distal end of the shaft, the second end effector element movable relative to the articulation; and the drive mechanism comprising a second actuator, the second actuator being connected to the second end effector element by a second pair of driving elements, the second pair of driving elements being configured such that a tension force applied by the second actuator to a first one of the second pair of driving elements causes the second end effector element to move relative to the articulation in the second motion direction, and the tension force applied to a second one of the second pair of driving elements causes the second end effector element to move relative to the articulation in the first motion direction; wherein the first one of the second pair of driving elements has a third path between the second actuator and the second end effector element, and the second one of the second pair of driving elements has a fourth path between the second actuator and the second end effector element, the third path having a lower tension force loss than the fourth path such that the second motion direction transfers a greater proportion of the tension force to the second end effector element than the first motion direction.

A contact length of the first path which contacts internal structure of the robotic surgical instrument may be less than a contact length of the second path which contacts internal structure of the robotic surgical instrument. A contact length of the third path which contacts internal structure of the robotic surgical instrument may be less than a contact length of the fourth path which contacts internal structure of the robotic surgical instrument.

An overall length of the first path may be less than an overall length of the second path. An overall length of the third path may be less than an overall length of the fourth path.

The first path may match the third path. The second path may match the fourth path.

The first one of the first pair of driving elements may be constrained to move around M pulleys, and the second one of the first pair of driving elements may be constrained to move around N pulleys, where M<N. In one example, M<N−1. For example, M=4 and N=6.

The first one of the second pair of driving elements may be constrained to move around J pulleys, and the second one of the second pair of driving elements may be constrained to move around K pulleys, where J<K. In one example, J<K−1. For example, M=J, and N=K.

The first one of the first pair of driving elements may have a larger diameter than the second one of the first pair of driving elements. The first one of the first pair of driving elements may be constructed of a smaller number of thicker strands than the second one of the first pair of driving elements.

The first one of the second pair of driving elements may have a larger diameter than the second one of the second pair of driving elements. The first one of the second pair of driving elements may be constructed of a smaller number of thicker strands than the second one of the second pair of driving elements.

Each driving element may comprise spokes.

Each driving element may be a cable.

Each driving element may resist compression and tension forces along its path.

The first and second one of each pair of driving elements may be integrally formed.

The first end effector element may be rotatable relative to the articulation about a first axis, and the first pair of driving elements may be configured such that the tension force applied by the first actuator to the first one of the first pair of driving elements causes the first end effector element to rotate about the first axis in a first rotation direction, and the tension force applied to the second one of the first pair of driving elements causes the first end effector element to rotate about the first axis in a second rotation direction.

The second end effector element may be rotatable relative to the articulation about the first axis, and the second pair of driving elements may be configured such that a tension force applied by the second actuator to the first one of the second pair of driving elements causes the second end effector element to rotate about the first axis in the second rotation direction, and the tension force applied to the second one of the second pair of driving elements causes the second end effector element to rotate about the first axis in the first rotation direction.

The robotic surgical instrument may be configured such that a tension force applied by the first actuator to the first one of the first pair of driving elements causes the first end effector element to rotate towards the second end effector element, and a tension force applied by the second actuator to the first one of the second pair of driving elements causes the second end effector element to rotate towards the first end effector element.

The robotic surgical instrument may be configured such that a tension force applied by the first actuator to the first one of the first pair of driving elements causes the first end effector element to rotate away from the second end effector element, and a tension force applied by the second actuator to the first one of the second pair of driving elements causes the second end effector element to rotate away from the first end effector element.

The first and second end effector elements may be opposing first and second jaws of an end effector.

The first end effector element may be linearly displaceable relative to the articulation, and the first pair of driving elements may be configured such that the tension force applied by the first actuator to the first one of the first pair of driving elements causes the first end effector element to linearly displace in a first linear direction, and the tension force applied to the second one of the first pair of driving elements causes the first end effector element to linearly displace in a second linear direction opposing the first linear direction.

The second end effector element may be linearly displaceable relative to the articulation, and the second pair of driving elements may be configured such that the tension force applied by the second actuator to the first one of the second pair of driving elements causes the second end effector element to linearly displace in the first linear direction, and the tension force applied to the second one of the second pair of driving elements causes the second end effector element to linearly displace in the second linear direction.

The first end effector element may be part of a stapler. The second end effector element may be part of a stapler.

BRIEF DESCRIPTION OF THE FIGURES

The present invention will now be described by way of example with reference to the accompanying drawings. In the drawings.

DETAILED DESCRIPTION

Figure 4:
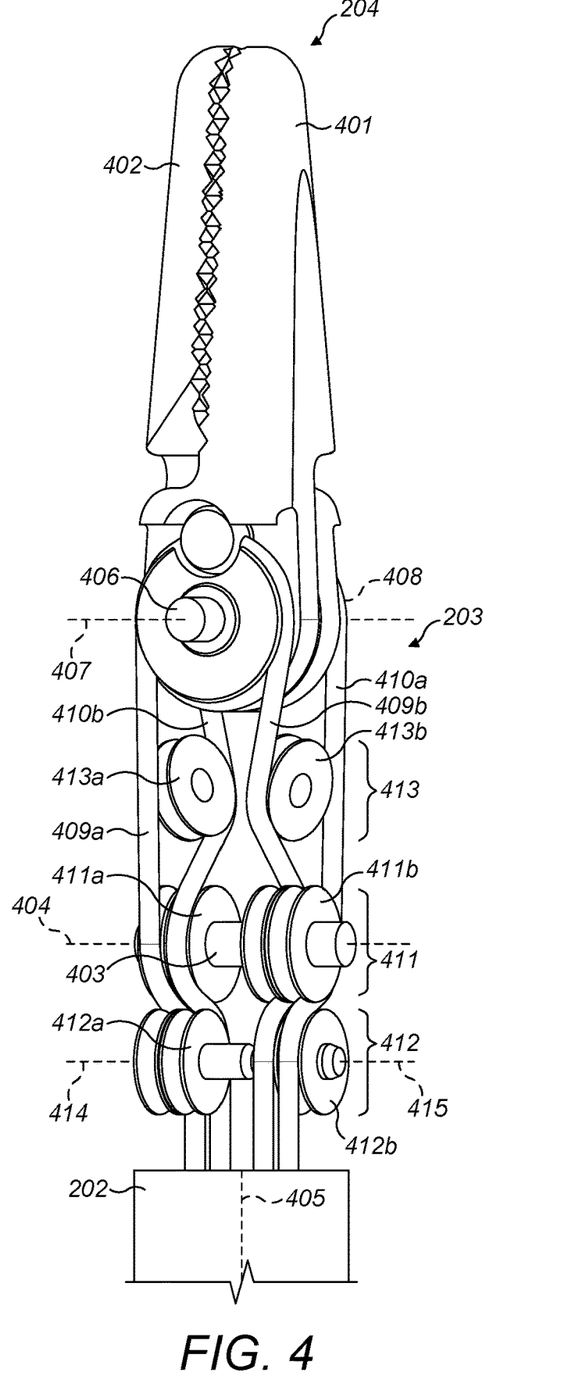
FIG. 4 illustrates an arrangement of the distal end of a surgical instrument.

FIG. 4 illustrates a schematic drawing of the distal end of an exemplary robotic surgical instrument. The surgical instrument as a whole has the general form shown in FIG. 2. In other words, the surgical instrument comprises a base 201 by which the surgical instrument connects to the surgical robot arm. The instrument base is designed cooperatively with the terminal end of the surgical robot arm, such that the instrument base is releasably attachable to the terminal end of the robot arm. A shaft 202 extends between the base 201 and an articulation 203. The articulation 203 is connected at its proximal end to the shaft 202 and at its distal end to an attachment suitable for attaching an end effector 204. The shaft 202 and articulation 203 are all hollow. This allows passage of driving elements up these sections to actuate the end effector 204. It also reduces the weight of the surgical instrument. The body of the articulation 203 is omitted from FIG. 4 for ease of illustration.

The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft.

The end effector of FIG. 4 has two opposing end effector elements 401 and 402, which are capable of cooperating so as to manipulate an object between them. The end effector may be of any suitable form able to function in this way. For example, the end effector may be any one of: smooth jaws, serrated jaws, a gripper, a pair of tweezers, a pair of shears, a pair of blades, a stapler, a clamp, a cauteriser. The end effector elements illustrated in FIG. 4 are opposing first 401 and second 402 jaws.

The articulation 203 comprises several joints which permit the end effector 204 to take a range of attitudes relative to the shaft 202 of the instrument. A first joint 403 (not fully shown) permits the end effector 204 as a whole to rotate about a first axis 404. This rotation is driven by driving elements (not shown). For example, the rotation may be cable driven. The first axis 404 is transverse to the longitudinal axis of the shaft 405.

A second joint 406 permits the first end effector element 401 to rotate about a second axis 407. The second axis 407 is transverse to the first axis 404. A first pair of driving elements 409a, 409b drives rotation of the first end effector element 401 about the second axis 407. The first pair of driving elements comprises a first driving element 409a and a second driving element 409b. Tension applied to the first driving element 409a causes the first end effector element 401 to rotate towards the second end effector element 402. Tension applied to the second driving element 409b causes the first end effector element 401 to rotate away from the second end effector element 402.

A third joint 408 permits the second end effector element 402 to rotate about the second axis 407. A second pair of driving elements 410a, 410b drives rotation of the second end effector element 402 about the second axis 407. The second pair of driving elements comprises a first driving element 410a and a second driving element 410b. Tension applied to the first driving element 410a causes the second end effector element 402 to rotate towards the first end effector element 401. Tension applied to the second driving element 410b causes the second end effector element 402 to rotate away from the first end effector element 401.

In the arrangement depicted in FIG. 4, each joint is driven by its own pair of driving elements. In other words, each joint is driven by a dedicated pair of driving elements. The joints are independently driven. The first end effector element 401 and the second end effector element 402 are independently rotatable about the second axis 407 by the second and third joints. Thus, the end effector elements may be rotated in the same direction or opposing directions by the second and third joints. The first end effector element 401 may be rotated about the second axis, whilst the second end effector element 402 is not rotated about the second axis. The second end effector element 402 may be rotated about the second axis, whilst the first end effector element 401 not rotated about the second axis.

FIG. 4 depicts the second joint 406 and the third joint 408 as permitting rotation about the same axis 407. However, the second and third joints may alternatively permit rotation of the end effector elements about different axes. The axis of rotation of one of the end effector elements may be offset in the longitudinal direction of the shaft 202 from the axis of rotation of the other end effector element. The axis of rotation of one of the end effector elements may be offset in a direction transverse to the longitudinal direction of the shaft 202 from the axis of rotation of the other end effector element. The axis of rotation of one of the end effector elements may not be parallel to the axis of rotation of the other end effector element. The axes of rotation of the end effector elements 401, 402 may be offset in the longitudinal direction of the shaft and/or offset in a direction perpendicular to the longitudinal direction of the shaft and/or angled with respect to each other. This may be desirable as a result of the end effector elements being asymmetric. For example, in an electrosurgical element, a first end effector element may be powered and a second end effector element not powered and insulated from the first end effector element. To aid this, the axes of rotation of the two end effector elements may be offset in the direction perpendicular to the longitudinal direction of the shaft. In another example, a first end effector element may be a blade and a second end effector element a flat cutting surface. To aid use of the blade, the axes of rotation of the two end effector elements may be angled to one another.

The surgical instrument of FIG. 4 further comprises a pulley arrangement around which the first and second pairs of driving elements 409a,b and 410a,b are constrained to move. The pulley arrangement comprises three sets of pulleys. A first set of pulleys 411 is rotatable about the first axis 404. Thus, the first set of pulleys 411 rotate about the same axis as the first joint 403. The first set of pulleys 411 comprises a pair of pulleys 411a and 411b located on either side of the first joint 403. The first and second pairs of driving elements are constrained to extend over the first joint 403 in order to reach the second and third joints 406, 408 respectively. The first one of the first pair of driving elements 409a passes over one side of pulley 411a and the second one of the first pair of driving elements 409b passes over the opposing side of pulley 411b so that whatever rotation there is of the end effector about first axis 404, the length of each one of the first pair of driving elements 409a, 409b is maintained the same. Similarly, the first one of the second pair of driving elements 410a passes over one side of pulley 411b and the second one of the second pair of driving elements 410b passes over the opposing side of pulley 411a so that whatever rotation there is of the end effector about first axis 404, the length of each one of the second pair of driving elements 410a, 410b is maintained the same.

The pulley arrangement further comprises a second set of pulleys 412. The first set of pulleys 411 are located between the second set of pulleys 412 and the end effector 204. The second set of pulleys 412 comprise a pair of pulleys 412a and 412b located on either side of the first joint 403. The first pulley 412a is rotatable about a third axis 414 which is parallel to the first axis 404. The third axis 414 may be offset from the first axis 404 both in the longitudinal direction of the shaft and also transverse to the longitudinal direction of the shaft. The second pulley 412b is rotatable about a fourth axis 415 which is parallel to the first axis 404. The fourth axis 415 is offset from the first axis 404 both in the longitudinal direction of the shaft and also transverse to the longitudinal direction of the shaft. The third and fourth axes are parallel but offset from each other. The third axis 414 and fourth axis 415 are in the same plane perpendicular to the longitudinal direction of the shaft. By offsetting the first pulley 412a and the second pulley 412b, the driving element wrapped around each pulley is able to extend down the shaft after having wrapped around the pulley. The first and second pairs of driving elements each are constrained to wrap around opposing sides of pulleys 411a and 412a. The first and second pairs of driving elements each are constrained to wrap around opposing sides of pulleys 412a and 412b. This ensures that the first and second pairs of driving elements remain taut whatever the rotation of the end effector about the first axis 404.

The pulley arrangement further comprises a pair of redirecting pulleys 413a and 413b. The redirecting pulleys 413a and 413b are located between the first set of pulleys 411 and the end effector 204. The redirecting pulleys are positioned so as to redirect the driving elements 409a, 409b from the first set of pulleys 411 to the second joint 406, and to redirect the driving elements 410a, 410b from the first set of pulleys 411 to the third joint 408. The redirecting pulleys ensure that the first and second pairs of driving elements maintain the same contact with the second and third joints whatever rotation there is of the end effector about the first axis 404. In other words, the first and second pairs of driving elements maintain the same amount of wrap around the second and third joints whatever the configuration of the instrument. This in turn ensures that the rotational range able to be imparted to the second and third joints by the first and second pairs of driving elements is maintained the same regardless of the pose position of the end effector.

The pulley arrangement ensures that in every configuration of the surgical instrument, the first and second pairs of driving elements remain taut, do not snag on the articulation or each other, and maintain sufficient wrap around the second and third joints. By avoiding slack in the driving elements, there is no backlash when articulating the joints of the surgical instrument. Thus, full control of the movement of the surgical instrument is achieved in every configuration of the surgical instrument. Alternative pulley arrangements to those illustrated in FIG. 4 may be utilised. Fewer or more pulleys may be used.

Figure 5:
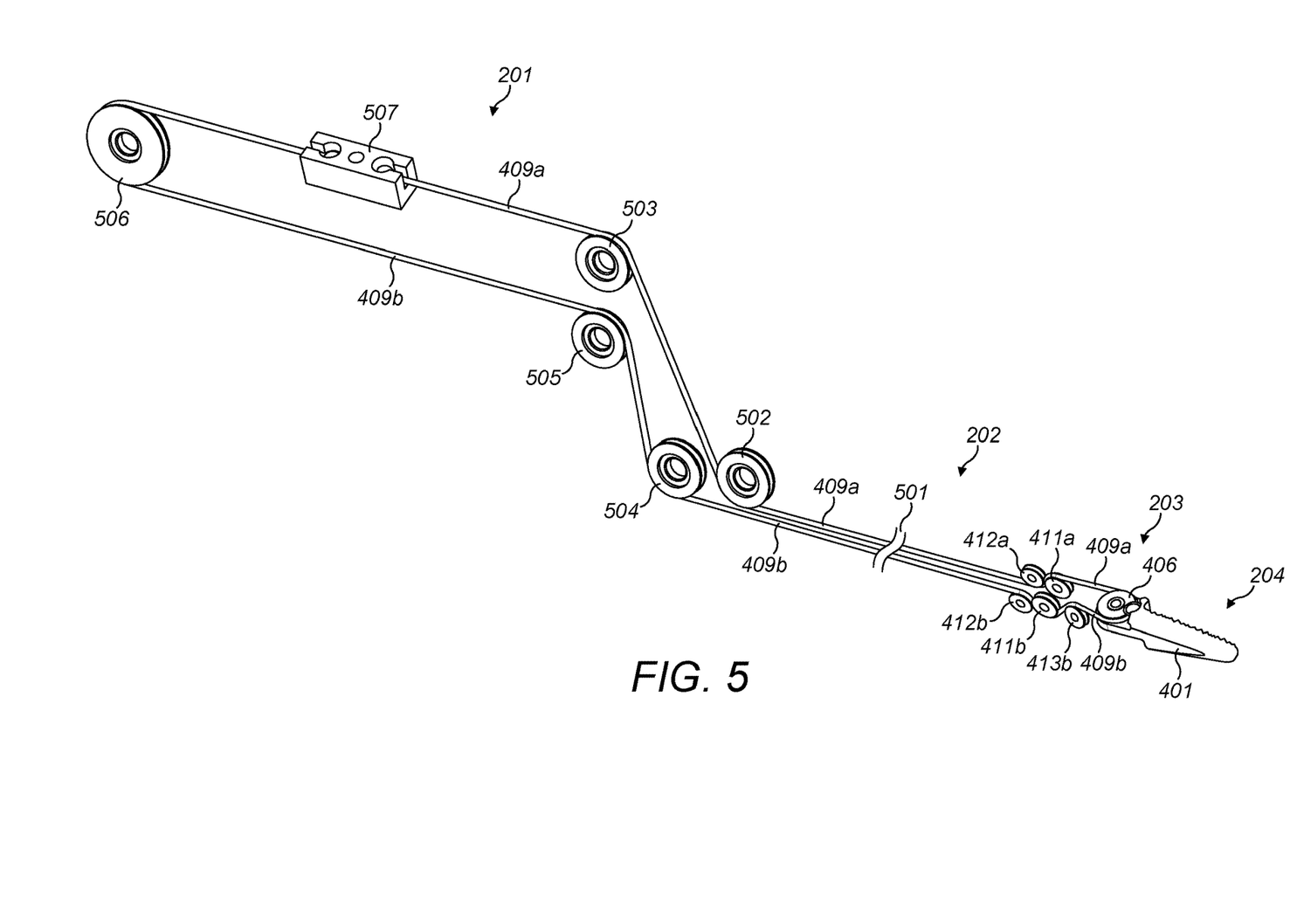
FIG. 5 illustrates a cable path for driving one jaw of the articulated end effector of FIG. 4.

FIG. 5 illustrates the path of the first pair of driving elements 409a, 409b in the surgical instrument. Only the first pair of driving elements and the components that the first pair of driving elements come into contact with are illustrated. The distal end of the instrument comprising articulation 203 and end effector element 401 is as described with respect to FIG. 4. The extent of the driving elements down the shaft 202 is not fully depicted, but abbreviated as indicated at 501. The remainder of the instrument structure that the first pair of driving elements contacts is in the instrument interface at the proximal end of the instrument 201.

The instrument interface comprises a drive mechanism for transferring drive from the robot arm to the driving elements. The drive mechanism comprises a plurality of actuators. Each actuator is secured to a pair of driving elements. In FIG. 5, first actuator 507 is secured to the first pair of driving elements 409a, 409b. Each actuator is secured to an instrument interface element (not shown on FIG. 5). Each instrument interface element engages a corresponding drive assembly interface element of the robot arm. Each actuator is linearly displaceable. Thus, the robot arm transfers drive to the end effector element as follows: movement of a drive assembly interface element moves an instrument interface element which moves an actuator which moves a driving element which moves a joint of the articulation which moves the end effector element. The first one of the first pair of driving elements 409a is constrained to move around pulleys 502 and 503 in the instrument interface. The second one of the first pair of driving elements 409b is constrained to move around pulleys 504, 505 and 506 in the instrument interface. These pulleys act to direct the first pair of driving elements from the shaft 202 to the first actuator 507.

Figure 6:
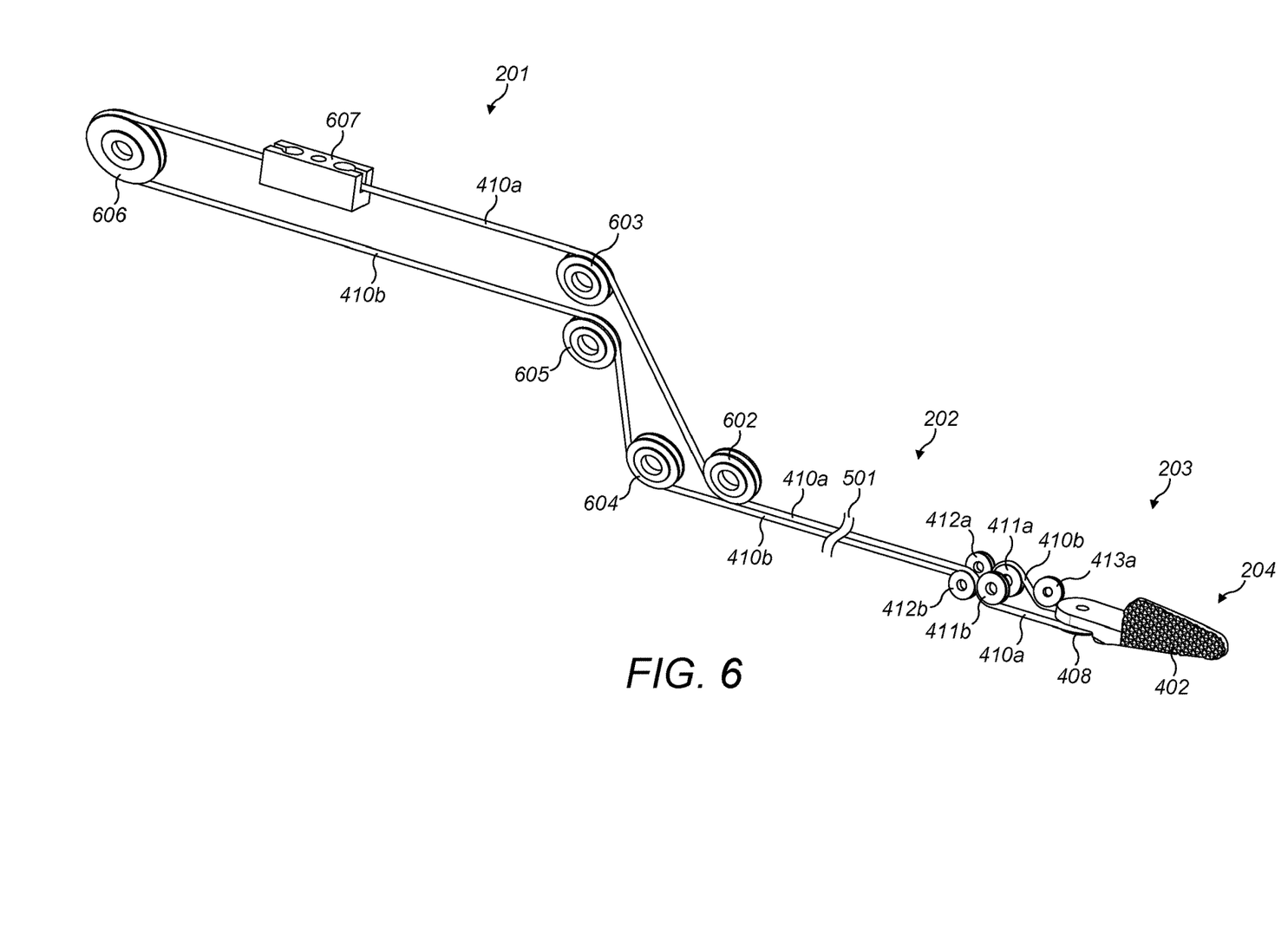
FIG. 6 illustrates a cable path for driving the other jaw of the articulated end effector of FIG. 4.

FIG. 6 illustrates the path of the second pair of driving elements 410a, 410b in the surgical instrument. Only the second pair of driving elements and the components that the second pair of driving elements come into contact with are illustrated. The distal end of the instrument comprising articulation 203 and end effector element 402 is as described with respect to FIG. 4. The extent of the driving elements down the shaft 202 is not fully depicted, but abbreviated as indicated at 501. The remainder of the instrument structure that the second pair of driving elements contacts is in the instrument interface at the proximal end of the instrument 201.

Second actuator 607 of the drive mechanism in the proximal end of the instrument 201 is secured to the second pair of driving elements 410a, 410b. The first one of the second pair of driving elements 410a is constrained to move around pulleys 602 and 603 in the instrument interface. The second one of the second pair of driving elements 410b is constrained to move around pulleys 604, 605 and 606 in the instrument interface. These pulleys act to direct the second pair of driving elements from the shaft 202 to the second actuator 607.

Figure 7:
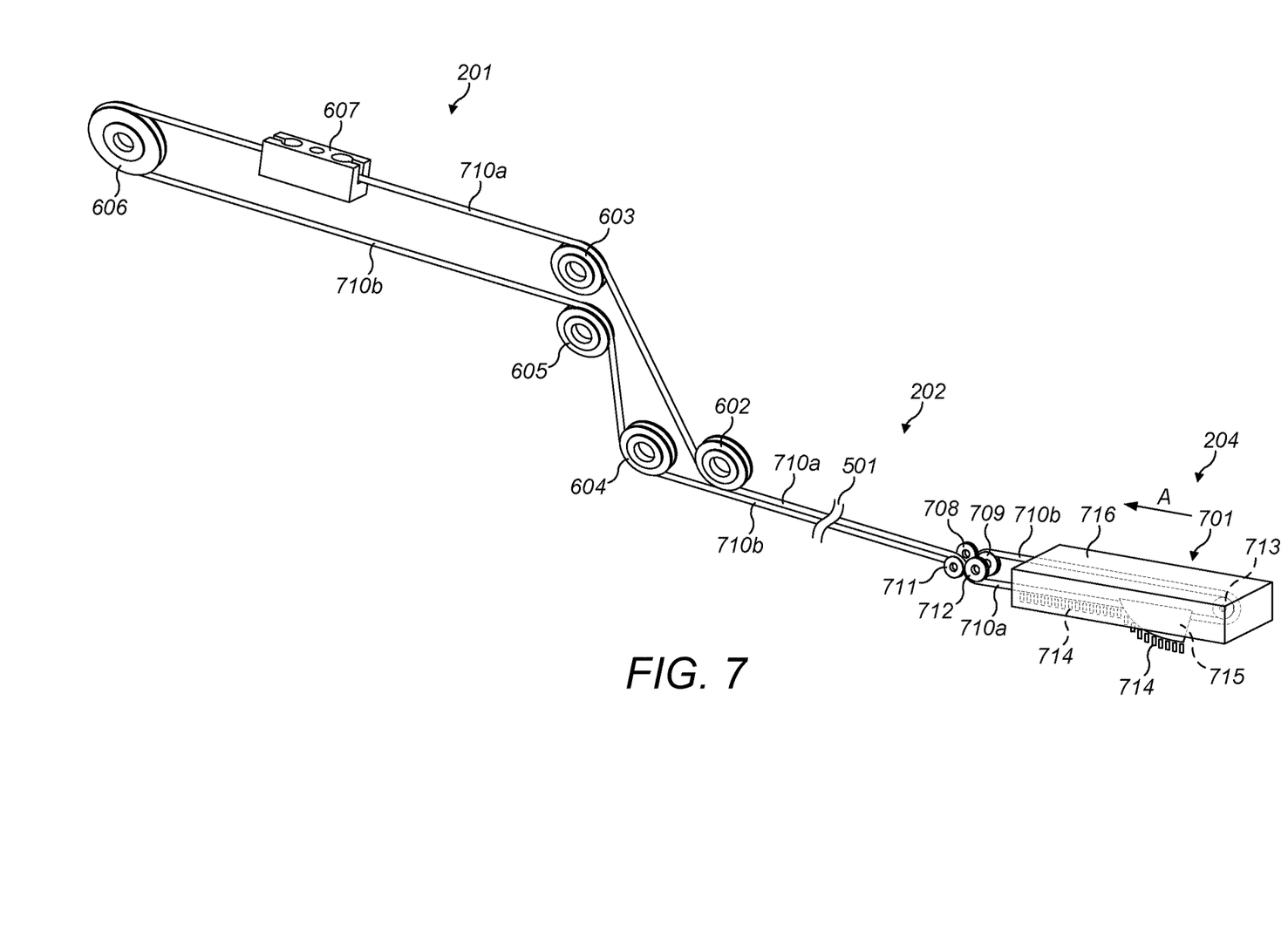
FIG. 7 illustrates a cable path for driving the linear displacement of a stapler applicator.
Figure 8:
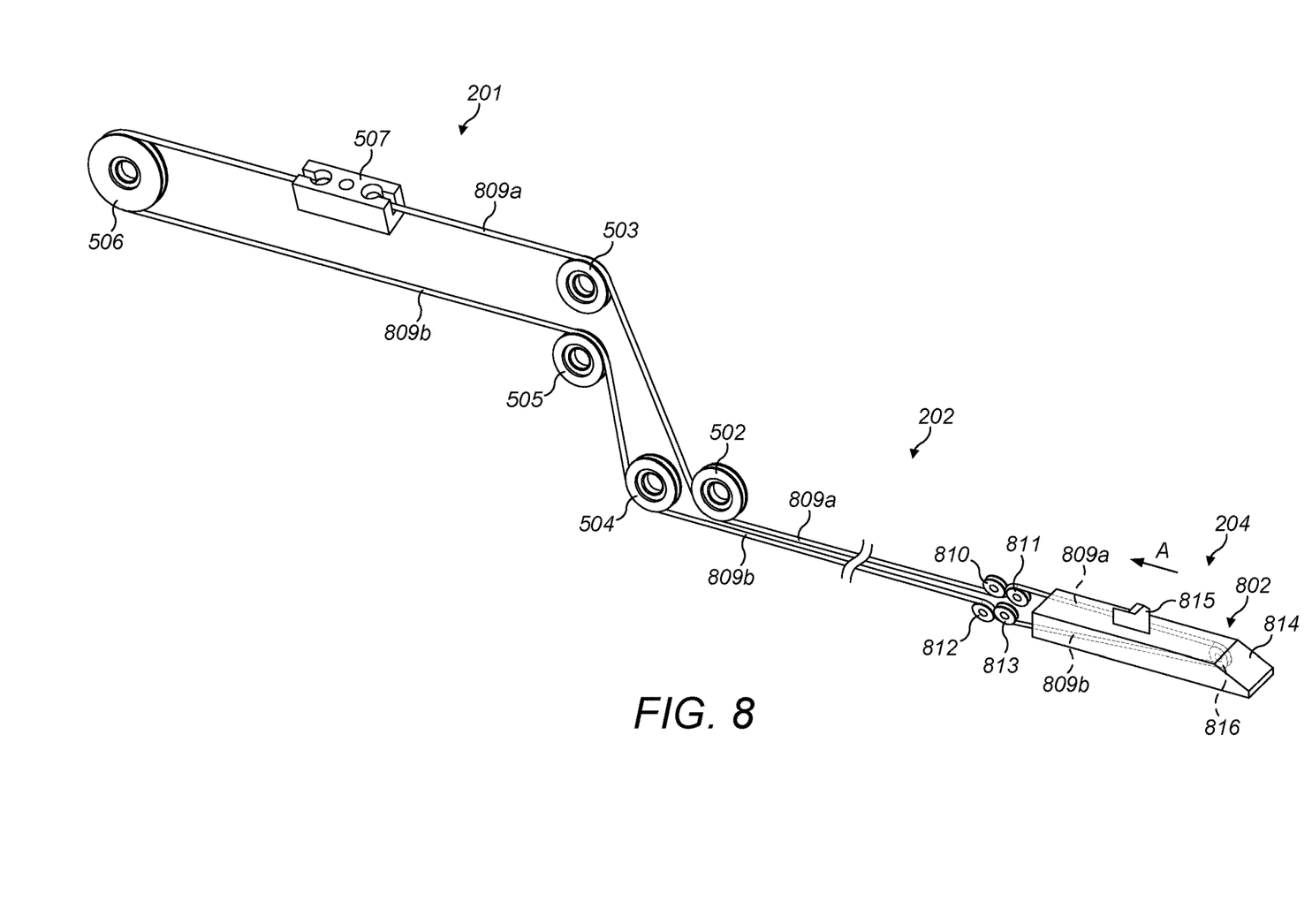
FIG. 8 illustrates a cable path for driving the linear displacement of a stapler blade.

FIGS. 7 and 8 illustrate the paths of pairs of driving elements 710a, 710b and 809a, 809b which are used to drive the motion of a stapler end effector. The stapler end effector comprises a first end effector part 701 and a second end effector part 802. The first end effector part 701 comprises a stapler block 716 which houses a bank of staples 714. The first end effector part 701 also comprises a stapler applicator 715. Driving elements 710a and 710b pass from the articulation into the stapler block 716 and terminate at either end of the stapler applicator 715. The driving elements 710a and 710b are rigidly attached to the stapler applicator 715. The driving elements wrap around pulley 713 at the distal end of the stapler block 716. The stapler applicator 715 is linearly displaceable within the stapler block 716. For example, the stapler applicator 715 may be permitted to slide within a channel or along a rail in the stapler block 716. The stapler applicator 715 is linearly displaceable relative to the articulation. The stapler applicator 715 is moveable in the direction marked by the arrow A, and in the opposing direction to A. The stapler applicator 715 engages the staples 714 as it moves. This causes the staples 714 to become exposed outside the stapler block 716. The staples are caused to close as a result of the stapler block being pressed against another item.

The second end effector part 802 comprises a stapler block 814 which houses a stapler blade 815. Driving elements 809a and 809b pass from the articulation into the stapler block 814 and terminate at either end of the stapler blade 815. The driving elements 809a and 809b are rigidly attached to the stapler blade 815. The driving elements wrap around pulley 816 at the distal end of the stapler block 814. The stapler blade 815 is linearly displaceable within the stapler block 814. For example, the stapler blade 815 may be permitted to slide within a channel or along a rail in the stapler block 814. The stapler blade 815 is linearly displaceable relative to the articulation. The stapler blade 815 is moveable in the direction marked by the arrow A, and in the opposing direction to A. The stapler blade 815 is exposed outside the stapler block 814.

In operation, tissue is clamped between the stapler block 814 and the stapler block 716. The stapler applicator 715 is drawn from the distal end of the stapler end effector part 701 to the proximal end of the stapler end effector part 701 by tensioning driving element 710a. The stapler applicator 715 engages the staples 714 causing them to be exposed outside the stapler block 716 and into the tissue clamped between the end effector parts. The staples penetrate through the tissue and are closed as they press against the other stapler block 814. The stapler blade 815 is drawn from the distal end of the stapler end effector part 802 to the proximal end of the stapler end effector part 802 by tensioning driving element 809a. This causes the stapler blade 815 to cut through the tissue clamped between the two end effector parts.

In FIGS. 7 and 8, each driving element is shown as wrapping around two pulleys in the articulation. For driving element 809a, these are pulleys 810 and 811. For driving element 809b, these are pulleys 812 and 813. For driving element 710a, these are pulleys 711 and 712. For driving element 710b, these are pulleys 708 and 709. These pulleys enable the end effector to rotate relative to the shaft of the instrument, as described with reference to pulleys 411a, 411b, 412a and 412b of FIGS. 4 to 6. Further pulleys may be used to enable further degrees of freedom of movement of the stapler end effector relative to the instrument shaft. One, or both, of the end effector parts 701 and 802 may be rotatable relative to the other end effector part. This may be implemented by incorporating a joint equivalent to joint 406 on one or each end effector part, and a further pair of driving elements to wrap around that joint, so as to permit rotation of the end effector part relative to the articulation about the joint. This thereby enables the end effector parts to open and close relative to each other, to thereby clamp material between them.

As with FIGS. 5 and 6, FIGS. 7 and 8 only illustrate those components of the instrument which the driving elements come into contact with. The extent of the driving elements down the shaft has been abbreviated, as indicated at 501. The internal structure of the instrument of FIGS. 7 and 8 at the proximal end of the instrument is as described with reference to FIGS. 5 and 6. The drive mechanism, and its connection to the drive assembly interface of the robot arm, operates as described with reference to FIGS. 5 and 6.

In FIGS. 7 and 8, the stapling and cutting actions are implemented by drawing the stapler applicator 715 and stapler blade 815 from the distal end of the end effector to the proximal end of the end effector in the direction labelled A on FIGS. 7 and 8. In an alternative implementation, the stapling and cutting actions are implementing by drawing the stapler applicator 715 and stapler blade 815 from the proximal end of the end effector to the distal end of the end effector in the opposite direction to that labelled A on FIGS. 7 and 8. Alternatively, one of the stapler applicator 715 and stapler blade 815 may be actioned by drawing it from the distal end to the proximal end of the end effector, and the other one of the stapler applicator 715 and stapler blade 815 actioned by drawing it from the proximal end to the distal end of the end effector.

The driving elements of FIGS. 4 to 8 are elongate elements which extend from the joints in the articulation 203 through the shaft to the instrument interface 201. Suitably, each driving element can be flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements are not flexible along their main extents. The driving elements resist compression and tension forces applied along their length. In other words, the driving elements resist compression and tension forces acting in the direction of their longitudinal axes. Thus, the driving elements are able to transfer drive from the instrument interface to the joints of the articulation. The driving elements may be cables.

Each pair of driving elements may be a uniform component having the same shape and size along its length and constructed of the same material along its length. Alternatively, each pair of driving elements may be composed of different portions. In one example, the portion of a driving element which engages components of the instrument interface (such as pulleys and interface elements) is flexible. For example, it may be a cable. Similarly, the portion of the driving element which engages components of the distal end of the surgical instrument (such as the pulleys and joints in the articulation) is flexible. For example, it may be a cable. Between these two flexible portions are spokes. Thus, in this example, each pair of driving elements comprises two spokes and two flexible portions. Each pair of driving elements forms a loop. The loop comprises alternating spokes and flexible portions. The two spokes are predominantly or wholly enclosed in the instrument shaft. A distal flexible portion terminates at one end in the distal end of one of the spokes, and at the other end in the distal end of the other spoke. The distal flexible portion engages components of the articulation. A proximal flexible portion terminates at one end in the proximal end of one of the spokes, and at the other end in the proximal end of the other spoke. The proximal flexible portion engages components of the instrument interface. The spokes are stiffer than the flexible portions. Suitably, the spokes are rigid. The spokes may be hollow tubes. Typically, the spokes have a larger diameter than the flexible portions. The flexible portions may terminate where they meet the spokes. Alternatively, the spokes may encapsulate the material of the flexible portions. For example, the spokes may be rigid sheaths which cover flexible cables.

In FIGS. 4 to 6, the first pair of driving elements 409a, 409b is secured to the second joint 406. For example, in FIG. 4, the first pair of driving elements is secured to the second joint with a ball and crimp termination. The first pair of driving elements is also secured to the first actuator 507. The first pair of driving elements may be integrally formed. For example, they may be a continuous cable. Alternatively, the first pair of driving elements may be disconnected where they are secured to the second joint and/or where they are secured to the first actuator.

The second pair of driving elements 410a, 410b is secured to the third joint 408. For example, the second pair of driving elements may be secured to the second joint with a ball and crimp termination. The second pair of driving elements is also secured to the second actuator 607.

The second pair of driving elements may be integrally formed. For example, they may be a continuous cable. Alternatively, the second pair of driving elements may be disconnected where they are secured to the third joint and/or where they are secured to the second actuator.

In FIG. 8, driving elements 809a and 809b are secured to the first actuator 507, and also secured to the stapler blade 815. This pair of driving elements may be integrally formed. For example, they may be a continuous cable. Alternatively, this pair of driving elements may be disconnected where they are secured to the stapler blade 815 and/or where they are secured to the first actuator 507.

In FIG. 7, driving elements 710a and 710b are secured to the second actuator 607, and also secured to stapler applicator 715. This pair of driving elements may be integrally formed. For example, they may be a continuous cable. Alternatively, this pair of driving elements may be disconnected where they are secured to the stapler applicator 715 and/or where they are secured to the second actuator 607.

The driving elements resist tension forces acting along their length. Thus, when an actuator is driven by the drive assembly, it applies a tension force to the driving element. In the case of FIGS. 5 and 6, this causes a rotational force to be applied to the joint it terminates at in the articulation. This causes the end effector element to rotate with the rotational force. In the case of FIGS. 7 and 8, this causes a linear force to be applied to the end effector element (stapler blade 815/stapler applicator 715). The rotational/linear force of the end effector element is not as large as the tension force applied to the driving element in the instrument interface due to a loss in tension of the driving element. This loss in tension force is primarily caused by friction between the driving element and the pulleys that it is constrained to move around between the actuator and the joint it is driving.

If both ones of a pair of driving elements are constructed the same and have paths which have the same number and size of pulleys, the same amount of wrap around the pulleys, and the same changes in direction around the pulleys, then the tension force loss in both driving elements of the pair is the same. Thus, the maximum motion (rotational or linear) force which is imparted to the end effector element is the same for both motion directions of the end effector element.

In the examples described herein, the paths of each of the driving elements of a pair of driving elements between the actuator and the joint they are driving are asymmetric. As a result of this, the maximum motion force which is imparted to the end effector element is different for the two motion directions of the end effector element. For each end effector, there is a priority motion direction for each end effector element. This priority motion direction is the direction which it is most important has the maximum tension force transferred to it by the driving mechanism of the instrument.

In the example of FIG. 4, the end effector is a pair of jaws. The jaws are used to grasp objects between them, thus the priority rotational direction for each jaw is that which effects the closing of the jaws together. The force with which the jaws are able to open is not as important. Thus, the priority rotational direction for the first jaw 401 is towards the second jaw 402, and the priority rotational direction for the second jaw 402 is towards the first jaw 401.

For other end effectors, the priority rotational direction for each end effector element may be that which effects the opening of the end effector elements away from each other. For example, an end effector which is a clamp may comprise two clamping end effector elements which hold apart two sections of tissue to maintain an opening. Another instrument may then manipulate the site inside the opening maintained by the clamp. In this case, the priority rotational direction for each clamping end effector element is away from the other clamping end effector element. In another example, an end effector may apply a clip or ligature into the surgical site. The clip or ligature is biased closed. The end effector applies force to open or hold open the clip or ligature to position it in the surgical site. In this case, the priority rotational direction for each end effector element is away from the other end effector element.

In the example of FIGS. 7 and 8, the end effector is a stapler. The two end effector parts are used to staple tissue clamped between them and then sever that tissue using the blade. The priority linear direction for each end effector part is that which effects the stapling action and the blade action. In other words, the priority linear direction for both the stapler blade 815 and the stapler applicator 715 in the arrangement depicted in FIGS. 7 and 8 is towards the articulation from the distal end of the end effector in the direction A. The force with which the stapler blade and the stapler applicator reset to their original positions is not as important.

If the blade and stapler were to operate so as to cut and staple in the opposite direction to that shown in FIGS. 7 and 8, then the priority linear direction would be the direction opposite to A.

The driving element of the first pair of driving elements that tension is applied to to effect motion of the first end effector element in the priority motion direction may have a symmetrical path to the driving element of the second pair of driving elements that tension is applied to to effect motion of the second end effector element in the priority motion direction. The driving element of the first pair of driving elements that tension is applied to to effect motion of the first end effector element in the non-priority motion direction may have a symmetrical path to the driving element of the second pair of driving elements that tension is applied to to effect motion of the second end effector element in the non-priority motion direction. In the example of FIGS. 5 and 6, the paths of driving element 409*a* and driving element 410*a* are symmetrical. And the paths of driving element 409*b* and driving element 410*b* are symmetrical. Thus, the closing force of each of the two jaws 401 and 402 is the same, and the opening force of each of the two jaws 401 and 402 is the same.

The position of the end effector relative to the terminal link of the robot arm may be determined by measuring the displacement of the actuators 507, 607 or by measuring the displacement of the instrument interface elements secured to the actuators, or by measuring the displacement of the drive assembly interface elements engaged with the instrument interface elements. Each displacement is measured using a position sensor which has a fixed position relative to the terminal link of the robot arm. Each sensed position can be used in combination with the other sensed positions, the known configuration of the internal structure of the instrument (pulleys etc) about which the driving elements are constrained to move, the lengths of the driving elements, and the shape and size of the end effector elements, to determine the position of the end effector relative to the terminal link of the robot arm.

In the examples described herein, the paths of each of the driving elements of a pair of driving elements between the actuator and the element they are driving are asymmetric. The determination of the end effector position using the above mechanism assumes that the lengths of the driving elements remain static. Any change to the length of the driving element caused by its interaction with the internal structure of the instrument (pulleys etc) or as a result of it stretching, will reduce the accuracy of the determined end effector element position. The longer the driving element, the more inaccurate the end effector element position determined in this manner. The more internal structure over which the driving element is constrained to move, the more inaccurate the end effector element position determined in this manner. The priority motion direction may be chosen to be the direction which it is most important has the most accurate sensed position of the end effector element.

For each pair of driving elements, the path of the driving element which is tensioned to effect motion of the end effector element in the priority motion direction has a lower tension force loss than the path of the driving element which is tensioned to effect motion of the end effector element in the opposing non-priority motion direction. This may be achieved using any one or combination of the following:

1. The path of the driving element which is tensioned to effect motion of the end effector element in the priority motion direction is constrained to move over M pulleys and the path of the driving element which is tensioned to effect motion of the end effector element in the opposing non-priority motion direction is constrained to move over N pulleys, where M<N. Suitably, M<N−1. Suitably, for an end effector 204, M for the first end effector element is the same as M for the second end effector element.

In the example of FIGS. 5 and 6, the first one of the first pair of driving elements which effects the closing of jaw 401 is constrained to move over four pulleys between the first actuator 507 and the second joint 406, whereas the second one of the first pair of driving elements which effects the opening of jaw 401 is constrained to move over six pulleys between the first actuator 507 and the second joint 406. Similarly, the first one of the second pair of driving elements which effects the closing of jaw 402 is constrained to move over four pulleys between the second actuator 607 and the third joint 408, whereas the second one of the second pair of driving elements which effects the opening of jaw 402 is constrained to move over six pulleys between the second actuator 507 and the third joint 408.

In the example of FIG. 7, the first one of the pair of driving elements 710a which, when tensioned, effects the stapling action is constrained to move over four pulleys between the second actuator 607 and the stapler applicator 715, whereas the second one of the pair of driving elements 710b is constrained to move over six pulleys between the second actuator 607 and the stapler applicator. Similarly, the first one of the pair of driving elements 809a which, when tensioned, effects the cutting action is constrained to move over four pulleys between the first actuator 507 and the stapler blade 815, whereas the second one of the pair of driving elements 809b is constrained to move over six pulleys between the first actuator 507 and the stapler blade 815.

2. The path of the driving element which is tensioned to effect motion of the end effector element in the priority motion direction is constrained to have a smaller wrap length around pulleys than the path of the driving element which is tensioned to effect motion of the end effector element in the opposing non-priority motion direction. In other words, the total length of the driving element which is in contact with the pulleys is less for the path of the driving element which is tensioned to effect motion of the end effector element in the priority motion direction than for the other driving element. Hence, the friction that the driving element which is tensioned to effect motion of the end effector element in the priority motion direction is exposed to is less than the friction that the other driving element is exposed to. Suitably, for an end effector 204, the wrap lengths around the pulleys of both the driving elements 409a, 410a which are tensioned to effect rotation of the end effector elements 401, 402 in the priority rotational direction are the same, and the wrap lengths around the pulleys of both the driving elements 409b, 410b which are tensioned to effect rotation of the end effector elements 401, 402 in the opposing non-priority rotational direction are the same.

In the example of FIGS. 5 and 6 and 7 and 8, each pair of driving elements changes direction by 180° at the proximal end of the instrument. The first and second pairs of driving elements are constrained to move around pulleys 506 and 606 respectively to effect this change of direction. The wrap of the driving elements around these pulleys is greater than any of the other pulleys due to the direction change. This 180° change of direction is wholly on the path of the driving element which is tensioned to effect motion of the end effector element in the non-priority motion direction. In FIGS. 7 and 8, each pair of driving elements also changes direction by 180° at the distal end of the instrument in the end effector. The driving elements 809b and 710b are constrained to move around pulleys 816 and 713 respectively to effect this change of direction. The wrap of the driving elements around these pulleys is wholly on the path of the driving element which is tensioned to effect linear displacement of the end effector element in the non-priority linear direction.

3. The overall length of the path of the driving element which is tensioned to effect motion of the end effector element in the priority motion direction is shorter than the overall length of the path of the driving element which is tensioned to effect motion of the end effector element in the non-priority motion direction. Thus, any loss of tension force due to stretching of the driving element which occurs is lower on the priority path than the non-priority path.

4. The construction of the driving element which is tensioned to effect motion of the end effector element in the priority motion direction may be different to the construction of the driving element which is tensioned to effect motion of the end effector element in the non-priority motion direction. A driving element with a smaller diameter may be used for the driving element which effects motion of the end effector element in the non-priority motion direction than the other driving element. Using a thinner driving element uses less space inside the instrument. Space is very limited inside the instrument, particularly in the articulation 203. Thus, this allows space for a thicker driving element to be used for the other driving element. A thicker driving element is able to withstand a greater force before stretching or breaking than a thinner driving element. Thus, a thicker driving element is better suited to carrying load than a thinner driving element. Thinner driving elements are better suited to changes of direction involving smaller bend radii than thicker driving elements which may fray. Thus, a thinner driving element is better suited to a driving element path constrained to move around more pulleys.

5. A driving element constructed of a smaller number of thicker strands may be used for the driving element which effects motion of the end effector element in the priority motion direction than the other driving element. The other driving element is constructed of a larger number of thinner strands. Both driving elements may have the same cross sectional area. Both driving elements may have similar longitudinal stiffness and strength.

The driving element having the smaller number of thicker strands has a higher yield stress. Thus, this driving element is able to bear a greater force, and hence is better suited to carrying load. This driving element is therefore used on the priority path which transfers a greater force to the end effector element than the non-priority path. Suitably, this driving element is constrained to move over fewer pulleys and/or has a smaller wrap length around the pulleys as described in points 1 and 2 above. This driving element is less flexible and more susceptible to fraying that the driving element having the larger number of thinner strands, thus is more suited to a driving element path with fewer changes in direction and less contact with the internal structure of the instrument.

The driving element having the greater number of thinner strands has a lower yield stress. Thus, this driving element is not able to bear as much force as the driving element having the smaller number of thicker strands. This driving element is therefore used on the non-priority path. Suitably, this driving element is constrained to move over more pulleys and/or has a larger wrap length around the pulleys as described in points 1 and 2 above. This driving element is more flexible and less susceptible to fraying than the driving element having a smaller number of thicker strands. These qualities cause the driving element having a greater number of thinner strands to be better suited to a driving element path constrained to move around more pulleys and/or undergo more changes in direction. Due to its flexibility, these changes in direction can be via tighter radii. This driving element is therefore more suited to the non-priority path.

Any one or combination of these approaches may be used to configure an asymmetric driving mechanism for the instrument such that for a given number of joints, driving elements, and pulleys, the force transferred to the end effector for implementing the priority actuation (be it closing or opening, linear displacement in one direction or the other) is maximised at the cost of reducing the force transferred to the end effector for implementing the non-priority actuation.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument comprising:
a shaft;
a first end effector element;
an articulation connecting the first end effector element to a distal end of the shaft, the first end effector element movable relative to the articulation; and
a drive mechanism at a proximal end of the shaft comprising a first actuator, the first actuator being connected to the first end effector element by a first pair of driving elements, the first pair of driving elements being configured such that a tension force applied by the first actuator to a first one of the first pair of driving elements causes the first end effector element to move relative to the articulation in a first motion direction, and the tension force applied to a second one of the first pair of driving elements causes the first end effector element to move relative to the articulation in a second motion direction;
wherein the first one of the first pair of driving elements has a first path between the first actuator and the first end effector element, and the second one of the first pair of driving elements has a second path between the first actuator and the first end effector element, the first path having a lower tension force loss than the second path such that the first motion direction transfers a greater proportion of the tension force to the first end effector element than the second motion direction.

2. A robotic surgical instrument as claimed in claim 1, further comprising:
a second end effector element;
the articulation connecting the second end effector element to the distal end of the shaft, the second end effector element movable relative to the articulation; and
the drive mechanism comprising a second actuator, the second actuator being connected to the second end effector element by a second pair of driving elements, the second pair of driving elements being configured such that a tension force applied by the second actuator to a first one of the second pair of driving elements causes the second end effector element to move relative to the articulation in the second motion direction, and the tension force applied to a second one of the second pair of driving elements causes the second end effector element to move relative to the articulation in the first motion direction;
wherein the first one of the second pair of driving elements has a third path between the second actuator and the second end effector element, and the second one of the second pair of driving elements has a fourth path between the second actuator and the second end effector element, the third path having a lower tension force loss than the fourth path such that the second motion direction transfers a greater proportion of the tension force to the second end effector element than the first motion direction.

3. A robotic surgical instrument as claimed in claim 2, wherein a contact length of the third path which contacts internal structure of the robotic surgical instrument is less than a contact length of the fourth path which contacts internal structure of the robotic surgical instrument.

4. A robotic surgical instrument as claimed in claim 2, wherein an overall length of the third path is less than an overall length of the fourth path.

5. A robotic surgical instrument as claimed in claim 2, wherein the first path matches the third path and the second path matches the fourth path.

6. A robotic surgical instrument as claimed in claim 2, wherein the first one of the second pair of driving elements is constrained to move around J pulleys, and the second one of the second pair of driving elements is constrained to move around K pulleys, where J<K or J<K−1.

7. A robotic surgical instrument as claimed in claim 6, wherein M=J, and N=K.

8. A robotic surgical instrument as claimed in claim 2, wherein the first one of the second pair of driving elements has a larger diameter than the second one of the second pair of driving elements and/or wherein the first one of the second pair of driving elements is constructed of a smaller number of thicker strands than the second one of the second pair of driving elements.

9. A robotic surgical instrument as claimed in claim 2, wherein the first end effector element is rotatable relative to the articulation about a first axis, and the first pair of driving elements is configured such that the tension force applied by the first actuator to the first one of the first pair of driving elements causes the first end effector element to rotate about the first axis in a first rotation direction, and the tension force applied to the second one of the first pair of driving elements causes the first end effector element to rotate about the first axis in a second rotation direction and the second end effector element is rotatable relative to the articulation about the first axis, and the second pair of driving elements is configured such that a tension force applied by the second actuator to the first one of the second pair of driving elements causes the second end effector element to rotate about the first axis in the second rotation direction, and the tension force applied to the second one of the second pair of driving elements causes the second end effector element to rotate about the first axis in the first rotation direction.

10. A robotic surgical instrument as claimed in claim 9, configured such that a tension force applied by the first actuator to the first one of the first pair of driving elements causes the first end effector element to rotate towards the second end effector element, and a tension force applied by the second actuator to the first one of the second pair of driving elements causes the second end effector element to rotate towards the first end effector element.

11. A robotic surgical instrument as claimed in claim 9, configured such that a tension force applied by the first actuator to the first one of the first pair of driving elements causes the first end effector element to rotate away from the second end effector element, and a tension force applied by the second actuator to the first one of the second pair of driving elements causes the second end effector element to rotate away from the first end effector element.

12. A robotic surgical instrument as claimed in claim 9, wherein the first and second end effector elements are opposing first and second jaws of an end effector.

13. A robotic surgical instrument as claimed in claim 1, wherein a contact length of the first path which contacts internal structure of the robotic surgical instrument is less than a contact length of the second path which contacts internal structure of the robotic surgical instrument.

14. A robotic surgical instrument as claimed in claim 1, wherein an overall length of the first path is less than an overall length of the second path.

15. A robotic surgical instrument as claimed in claim 1, wherein the first one of the first pair of driving elements is constrained to move around M pulleys, and the second one of the first pair of driving elements is constrained to move around N pulleys, where M<N or M<N−1.

16. A robotic surgical instrument as claimed in claim 1, wherein the first one of the first pair of driving elements has a larger diameter than the second one of the first pair of driving elements and/or wherein the first one of the first pair of driving elements is constructed of a smaller number of thicker strands than the second one of the first pair of driving elements.

17. A robotic surgical instrument as claimed in claim 1, wherein the first and second one of each pair of driving elements are integrally formed.

18. A robotic surgical instrument as claimed in claim 1, wherein the first end effector element is linearly displaceable relative to the articulation, and the first pair of driving elements is configured such that the tension force applied by the first actuator to the first one of the first pair of driving elements causes the first end effector element to linearly displace in a first linear direction, and the tension force applied to the second one of the first pair of driving elements causes the first end effector element to linearly displace in a second linear direction opposing the first linear direction.

19. A robotic surgical instrument as claimed in claim 18, wherein the second end effector element is linearly displaceable relative to the articulation, and the second pair of driving elements is configured such that the tension force applied by the second actuator to the first one of the second pair of driving elements causes the second end effector element to linearly displace in the first linear direction, and the tension force applied to the second one of the second pair of driving elements causes the second end effector element to linearly displace in the second linear direction.

20. A robotic surgical instrument as claimed in claim 18, wherein the first end effector element is part of a stapler.

* * * * *